United States Patent [19]

Crock et al.

[11] 3,945,712

[45] Mar. 23, 1976

[54] OPERATING MAGNIFIER AND MINIATURE OPTHALMOSCOPE

[75] Inventors: Gerard William Crock, Kew; Ljubomir Pericic, Alphington, both of Australia

[73] Assignee: University of Melbourne, Melbourne, Australia

[22] Filed: May 31, 1974

[21] Appl. No.: 474,925

[52] U.S. Cl. .................. 351/6; 350/36; 350/38; 350/72; 351/16
[51] Int. Cl.² .................... A61B 3/12; G02B 25/02
[58] Field of Search ......... 350/145, 146, 36, 37, 38, 350/72; 351/6, 16

[56] References Cited
OTHER PUBLICATIONS

Keeler advertisement, *Amer. J. Ophthalmology*, May 1971.

*Primary Examiner*—Paul A. Sacher
*Attorney, Agent, or Firm*—Dennison, Dennison, Meserole & Pollack

[57] ABSTRACT

A magnifier and miniature ophthalmoscope which may be worn over the eyes of a surgeon and which permits use without removal from the head as either an ophthalmoscope or as a magnifier. A first optical path of the instrument includes a magnifying objective and an eyepiece. A second optical path which can be introduced includes a first silvered mirror directed toward the center of the instrument and a second silvered mirror on the instrument center line and an objective so that each eye of the wearer examines a narrow field at about the center line of the instrument. A change means in the form of a carriage carrying the eyepiece of the magnifier and the first mirror may be moved to select the instrument function.

5 Claims, 6 Drawing Figures

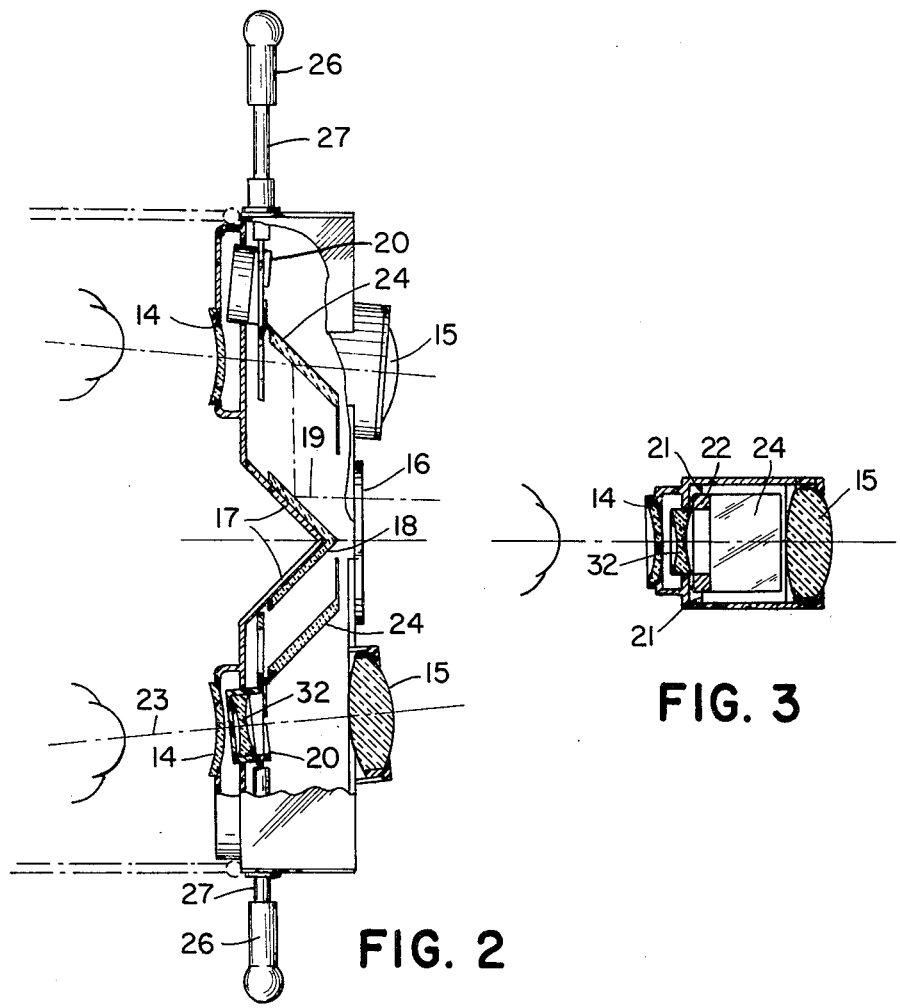
FIG. 3
FIG. 2
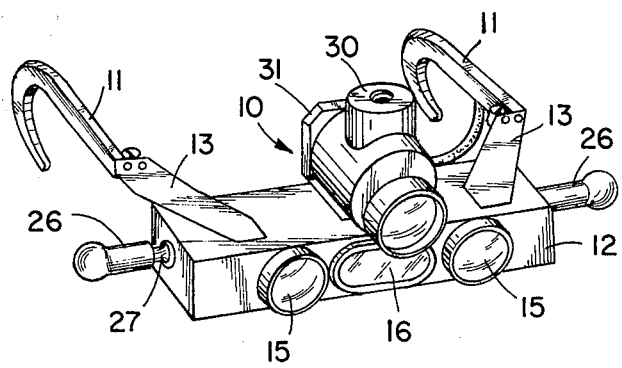
FIG. 1

OPERATING MAGNIFIER AND MINIATURE OPTHALMOSCOPE

This invention relates to an improved operating magnifier and miniature ophthalmoscope.

There are certain surgical procedures where it is required that the surgeon use a magnifier and there are other procedures where an indirect ophthalmoscope which gives, for example, a stereoscopic view of the area being examined, such as the fundus of the eye. In this specification, the term ophthalmoscope is to be construed as defining the general type of instrument rather than the type used by ophthalmic surgeons as similar instruments can be used in other fields.

Where an ophthalmic surgeon is operating and has to use both an ophthalmoscope and a magnifier this has previously been difficult and it has been necessary for the surgeon to have one instrument removed from before his eyes and the other replaced as and where necessary.

The object of the present invention is to provide a single unit which can, selectively, be used as an ophthalmoscope or as a magnifier.

The invention, in its broadest sense includes an operating magnifying miniature ophthalmoscope having means whereby the instrument can be worn by a user, a first optical path through the instrument having an objective and an eye piece, the objective being a magnifying lens and a second optical path which can be introduced which path comprises a first silvered mirror directed towards the centre of the instrument, a second parallel silvered mirror on the centre line of the instrument and an objective whereby each eye examines a very narrow field at about the centre line of the instrument.

Preferably the change mechanism between the first and second optical paths can comprise a carriage which carries the eye piece of the magnifier and the first silvered mirror, the carriage in one position permitting the magnifying function to be effected and in the other extreme condition sets up the ophthalmoscopic function.

The instrument of the invention may also have associated therewith a light source and preferably the working distance of the ophthalmoscope, the magnifier and the light source are all the same. The instrument may also be adapted to use with certain teaching instruments such as a teaching prism system where a student can ascertain the direction of view of a teacher. The light source may be provided with a filter which can be selectively positioned.

In order that the invention may be more readily understood and put into practice we shall describe one particular form of the invention, with reference to the accompanying drawings, in which:

FIG. 1 is a perspective view of the magnifier/ophthalmoscope made in accordance with the invention;

FIG. 2 is a horizontal section through the magnifier;

FIG. 3 is a vertical section through one eye piece of the magnifier/ophthalmoscope

Figure 4:
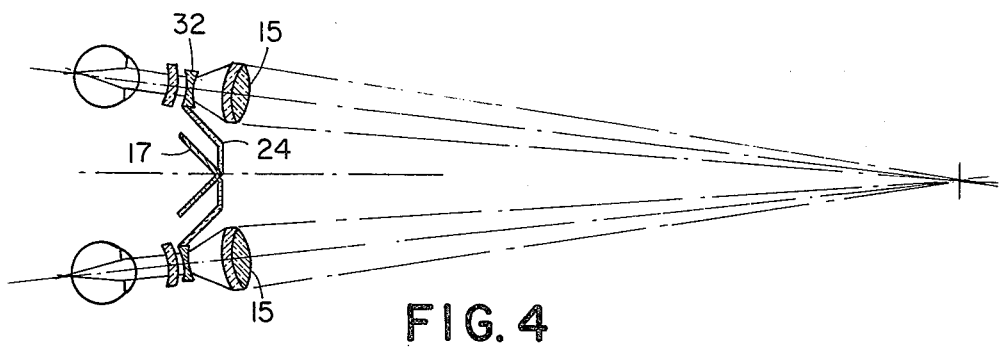
FIG. 4 is a schematic view of the instrument used as a magnifier.

In this form the instrument 10 is made with wings 11 adapted to be placed over the users ears and is also arranged to rest on the users nose. Alternatively the instrument could be formed on a conventional glasses frame and if required in the lower portions of the eye pieces of the frame optical glass may be provided so that a user who normally wears glasses can obtain clear vision through this portion.

The instrument may generally be considered in the form of a rectangular box 12, which may be made of metal. One preferred in the illustrated form the box has a pair of brackets 13 which extend outwardly and to which the wings are fitted.

The instrument is provided with eye pieces 14 which if required may be ground to the optical prescription of the user. Inwardly of the eye pieces there are a pair of objectives 15 which are directed slightly inwardly so as to provide a predetermined working distance of the instrument. In one preferred form this distance may be of the order of 12 inches. These objectives may be removeable so that different magnifications can be provided and in practice we find that magnifications are between two times to four times are satisfactory. Provided centrally of the front face of the instrument there is provided an objective or window 16 which is used when the instrument is operated as an ophthalmoscope, as will be described hereinafter.

Internally of the instrument and at the rear thereof the instrument is formed with a pair of planes 17 which may each lie at 45° through a vertical axis through the centre of the device. The planes so formed may be formed by pressing of the body of the instrument or in any other way. The outer surface of each of these planes is silvered by a deposition 18 and it will be seen that there is an optical path for example path 19 from the window 16 of the device to these planes 17 from whence the incident light is transmitted through 90° towards the ends of the instrument.

Mounted within the instrument there are a pair of carriages 20. The form of mounting of these carriages is not critical but they can be provided with grooves 22 along their upper and lower edges which move in corresponding knife edges 21 in or associated with the body of the instrument so that the movement of the carriages is carefully controlled.

Each of these carriages has adjacent its inner edge an eye piece 32 which comprises part of the lens system of the operating magnifier. The arrangement is such that when the carriage is moved fully inwardly, as at the lower portion of FIG. 2, there is a direct optical path 23 through the ground or planar glass 14 at the rear of the instrument, through the eye piece 32 and through the objective 15. The paths for each eye are such that they converge on the centre line of the instrument at the predetermined distance, say 12 inches. As and where required a stop is provided so that the objectives 15 are held in the required position.

Mounted on each side of the carriage 20 inwardly of the objectives 15 and extending forwardly are a pair of plates 24 which have silvered inner surfaces. When the carriages are moved to their fully extended condition, as shown in the top portion of FIG. 2, that is, when they are close to the ends of the instrument as possible, these plates are located in front of the position of viewing and thus there is a light path from this position along the body of the instrument towards the centre plane 17 and through the optical path 19 at the centre of the instrument. The arrangement is such that each side is symmetrical so that the working distance of each side and thus each eye is the same and we also arrange this as to be the same as the working distance of the magnifier.

Control of the carriages may be by means of finger grips or the like 26 attached to an extension 27 passing through each end of the ophthalmoscope so that the movement can be controlled by the fingers of a wearer. We provide stops, not illustrated, so that the movement in each direction is controlled and preferably the stops may be adjustable to account for wear in the instrument. In use the members by which the carriages are moved may well be provided with a sterile plastic tube or the like thereon which permits these members to be moved by the surgeon or an assistant during the operation in a sterile manner.

Figure 5:
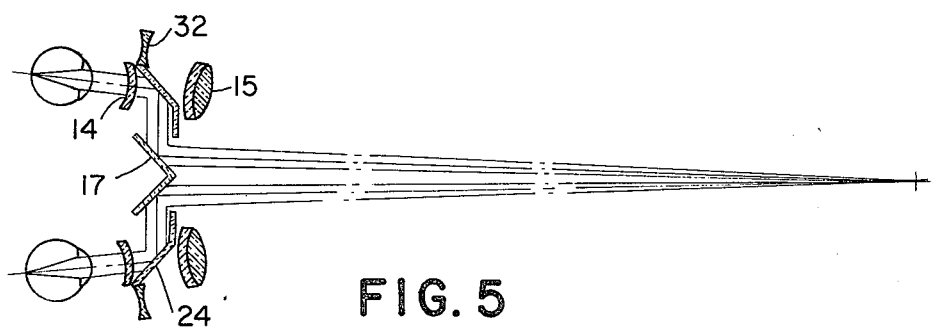
FIG. 5 is a schematic view of the instrument used as an ophthalmoscope.
Figure 6:
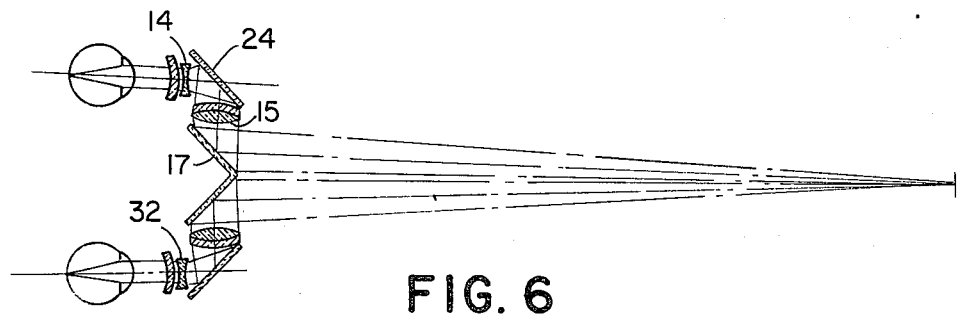
FIG. 6 is a schematic view of a modified form of the invention.

FIGS. 4 and 5 show the optical paths and the relative fields of vision when the instrument is used as a magnifier and ophthalmoscope, respectively. The form of the invention illustrated in FIG. 6 shows a modified optical system having a magnifying objective in the light path of the ophthalmoscope.

Mounted on the body or on the spectacle frame above the body there is a light source 30. This light source may show a miniature beam and may be provided so that the focus of this beam is at the working distance of the device. When a high powered light source is to be used a heat shield 31 can be located behind the light source.

Although not illustrated, in one particular form of the invention, we provide a light source which is pivotly attached to a pair of extensions from the instrument itself and which has a further pair of members passing through an arcuate groove and adapted to be clamped thereto. In this arrangement the angle of the light source relative to the centre line of the instrument can be adusted so that the light is effectively illuminating the working area.

Although this is not illustrated, the instrument can be arranged for use by persons having a pupillary distance which differs from the average.

Where an instrument is made for a particular surgeon the location of the eye pieces 32 can be varied, the stops on the carriages 20 varied, and the location of the objectives 15 adjusted to the correct spacing.

Alternatively, at least the eye piece 32 and the objective 15 can be built into a telescope with the whole of the unit being moveable. In this case the eye piece 14 would either be readily removeable so that a surgeon could insert his own prescription lens or it would be unground and simply act as a window.

In use, if the particular instrument permits, the surgeon selects the magnification required for use of the device as a magnifier and if it is to be so used both of the carriages are moved to their fully inward position. At this condition the surgeon looking through the instrument can see a magnified image at the working distance, say 12 inches.

If the instrument is to be used as an ophthalmoscope it is only necessary to move the extensions from the carriages outwardly and this causes the carriages to move along their track until they assume a position where there is a light path from the point of optimum working distance to one of the inclined silvered members formed in or associated with the back of the instrument, to the silvered member associated with the carriage and through the rear of the device. It can be seen that the transfer from one mode of operation to the other mode is extremely rapid and simple and can be effected either by the surgeon, an assistant or a nurse with very little difficulty. The form of construction described is also satisfactory in practice in that the main wearing surfaces, those associated with the carriages provide large distances of contact and thus wear is minimal, stops can be provided on the extensions through the body or in the body and these stops can if necessary, be adjustable to take into account anywhere and the general arrangement is such that the interior of the device remains clean and dust free for long periods.

The light source 30 may be of one of two general forms. In the first form the light source may be operated from a power pack or the like in which case the surgeon needs to carry a length of cable connected to the power pack. Alternatively, a portable battery power pack can be provided which permits the surgeon a greater degree of movement whilst using the device.

The device is also useful for teaching purposes. The central aperture, that associated with the ophthalmoscope, may be provided with a surround which has on one side either an angled silvered surface or if required an angled half silvered surface extending thereover. In each case a student may stand beside a surgeon and by viewing the angled surface can look at the point at which the surgeon is looking. As the working distance of the ophthalmoscope and magnifier are the same even if the surgeon is using the magnifier the mirror associated with the ophthalmoscope will show the same field of view. Also in some applications it is desirable to be able to provide a filter over the light source and we provide a pivotted arrangement whereby a filter may be clipped over the light source or removed therefrom as required. Also there may be provided with the instrument of the invention a special arrangement of aspheric condenser lenses which permit the viewer to obtain a fundus image. The lens is provided with a special flange which may be triangular in cross section with the base of the triangle being the outer surface of the angular flange and in this arrangement we have found that it is more simple to clean the lens than has previously been the case.

While the instrument is designed primarily for the use of Retinal Surgeons, it has wider applications in medicine and surgery; notably in Otorhinolaryngology and conceivably in Plastic Surgery, Neurosurgery, General Surgery of the Biliary System, Renal Transplantation and other small organ transplantation procedures and for gynaecological work to mention some of the other potential medical applications.

It may also have a place in dentistry and in veterinary science and in the meat inspection and packaging industry. It may also have an application in the area of industrial design and art work including security artists. Other industrial applications which come to mind would include watch making and possibly some of the coarser manufacturing stages in the electronic industry.

Whilst we have described one specific form of ophthalmoscope made in accordance with the invention it is to be understood that many modifications can be made to the specific components of the invention, to the actual form of the instrument when manufactured and to the form of movement of the carriages without departing from the spirit and scope of the invention.

I claim:

1. An operating magnifier and miniature ophthalmoscope having a body, means on the body for retaining the instrument on a user's head, two carriages mounted in the body, each carriage being movable between two positions, in the first position each carriage providing a first optical path through the instrument which path includes an objective and an eye piece, the objective being a magnifying lens, and in the second position each carriage providing a second optical path which path comprises a first silvered mirror directed towards the centre of the instrument, a second parallel silvered mirror on the centre line of the instrument and an objective.

2. An instrument as claimed in claim 1 wherein the carriages each carry the eye piece of the magnifier and the first silvered mirror.

3. An instrument as claimed in claim 1 having a second eye piece common to each optical path.

4. An instrument as claimed in claim 3 wherein the second eye piece is ground to the prescription lens of the user.

5. An instrument as claimed in claim 1 having associated therwith a light source, the working distance of the ophthalmoscope, the magnifier and the light source are the same.

* * * * *